United States Patent [19]

Ito

[11] 4,049,395
[45] Sept. 20, 1977

[54] METHOD FOR TREATING RAW MATERIAL WITH A TREATING GAS

[75] Inventor: Shozo Ito, Ichikawa, Japan

[73] Assignee: Mifuji Iron Works Co., Ltd., Japan

[21] Appl. No.: 614,617

[22] Filed: Sept. 18, 1975

Related U.S. Application Data

[60] Division of Ser. No. 546,737, Feb. 3, 1975, and a continuation-in-part of Ser. No. 823,746, May 12, 1969, abandoned.

[30] Foreign Application Priority Data

May 15, 1968 Japan .................................. 43-32170
June 20, 1968 Japan .................................. 43-42258

[51] Int. Cl.$^2$ ........................... C10J 3/00; C01B 2/14
[52] U.S. Cl. ..................................... 48/197 R; 48/210; 48/213; 48/215; 201/36; 208/46; 252/373; 252/445; 260/346.4
[58] Field of Search .................... 48/197 R, 212, 213, 48/215, 202, 206, 210; 252/373, 445, 421; 260/346.4, 687, 679; 201/36, 34, 31; 208/46; 23/277 R, 284, 262, 259.5, 288 S

[56] References Cited

U.S. PATENT DOCUMENTS

| | | | |
|---|---|---|---|
| 2,358,359 | 9/1944 | Stuart | 252/421 |
| 2,709,675 | 5/1955 | Phinney | 201/31 |
| 2,767,233 | 10/1956 | Mullen II et al | 48/212 |
| 3,254,976 | 6/1966 | Wolf et al. | 48/206 |
| 3,306,915 | 2/1967 | Harvey | 260/346.4 |
| 3,567,395 | 3/1971 | Henderson | 23/259.5 |
| 3,607,062 | 9/1971 | Sudduth | 201/36 |

*Primary Examiner*—Robert L. Lindsay, Jr.
*Assistant Examiner*—George C. Yeung
*Attorney, Agent, or Firm*—Robert E. Burns; Emmanuel J. Lobato; Bruce L. Adams

[57] ABSTRACT

A method for treating raw material comprises mixing fuel and air in a mixing chamber to produce a combustible mixture, ejecting the combustible mixture into a combustion chamber and burning it therein to evolve hot products of combustion which are fed directly into an adjoining conditioning chamber. Additional gas is supplied to the conditioning chamber and mixed with the products of combustion to form a conditioned treating gas having a prescribed temperature and composition. To promote rapid and uniform mixing of the gases and hence form a uniform treating gas, the conditioning chamber is connected directly to and has a volume 1½ to 6 times greater than that of the combustion chamber. A treating chamber disposed downstream from the conditioning chamber receives both the preconditioned treating gas and the raw material to be treated and the raw material is acted thereon by the treating gas while temporarily stored in the treating chamber.

12 Claims, 10 Drawing Figures

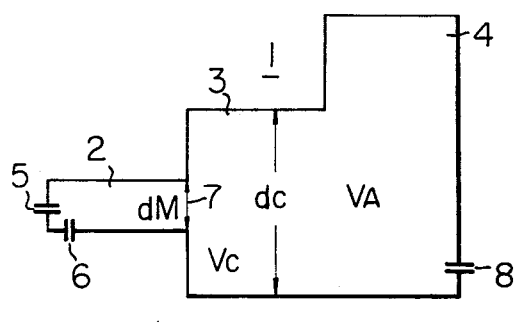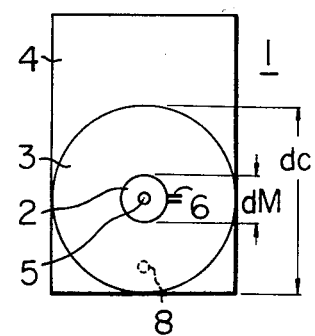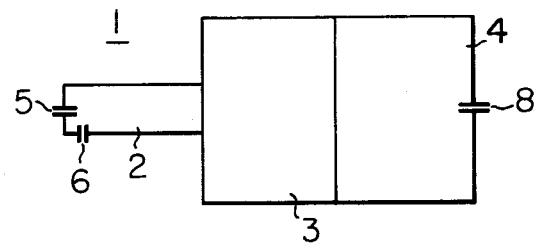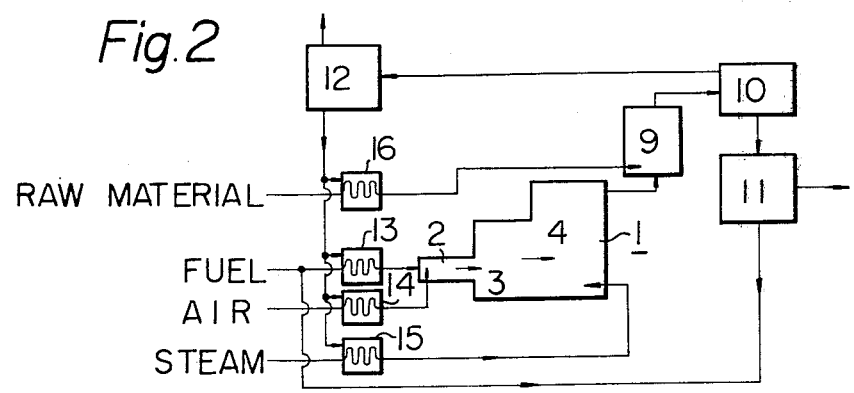

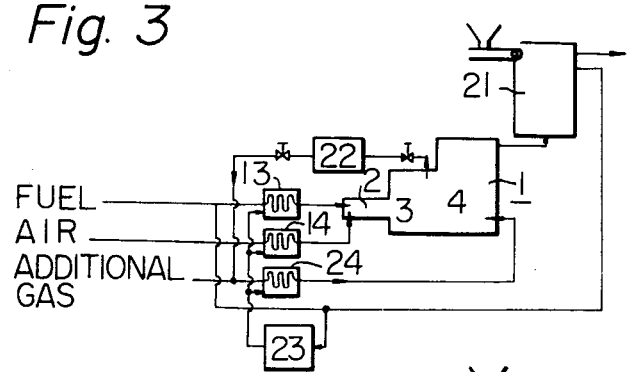
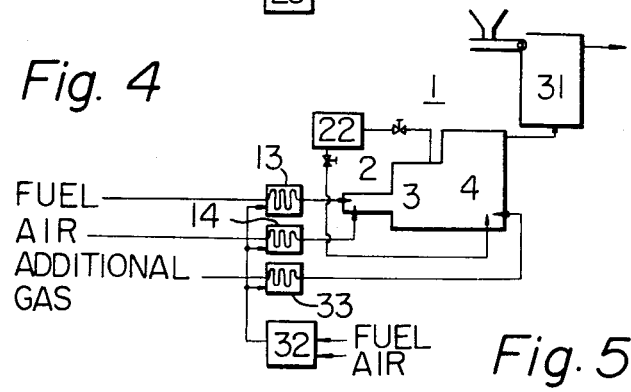
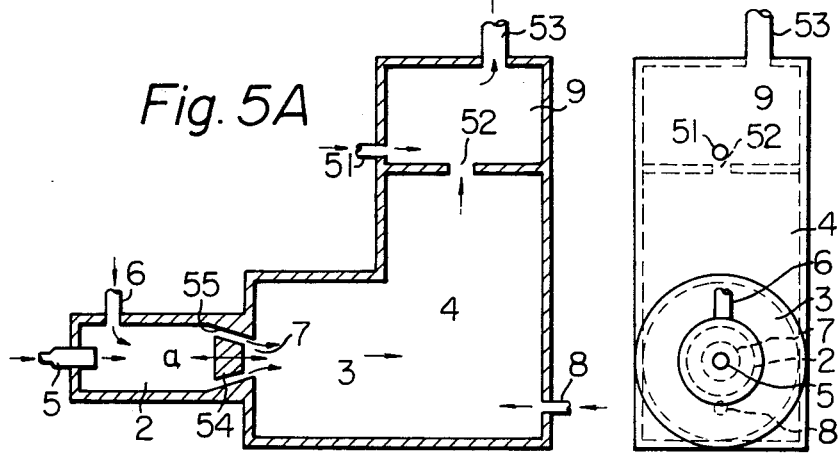

METHOD FOR TREATING RAW MATERIAL WITH A TREATING GAS

This is a divisional, of application Ser. No. 546,737, filed Feb. 3, 1975; which is a C-I-P of SN 823,746, filed May 12, 1969, now abandoned.

FIELD OF THE INVENTION

The present invention relates to an improved method for treating raw material with a treating gas, and more particularly, relates to an improved method for treating raw material with a treating gas which is suitably conditioned to a prescribed temperature and composition.

BACKGROUND OF THE INVENTION

There are numerous processes in the chemical industry and related fields in which a gas is heated to a high temperature and then used as the heat transfer medium or treating agent in a subsequent operation. For example, such operations include thermal decomposition processes for manufacturing fuel gas, town gas, synthetic gas, or raw material gas usable for synthetizing chemicals, such as ethylene, propylene and acetylene, from petroleum hydrocarbons; alteration processes for natural gas; distillation of coal, wood and various agricultural products for manufacturing carbonized products; oxidation processes for oxidizing metal ores, coal benzene and naphthalene; reduction processes for reducing metal oxides and ores; and activation processes for activating carbonized products.

Normally such processes are carried out by gigantic equipment on a large scale. Consequently, the following conditions must be satisfied in order to carry out such processes economically:

1. the treating condition must be maintained constant, i.e., the temperature and composition of the treating system must be maintained constant so that uniform quality products can be manufactured from the treating system,
2. easy and continuous operation,
3. low operating costs, and
4. simple and low cost equipment and maintenance.

However, all of the above requirements have not been successfully satisfied in the prior art methods and apparatuses in which raw material is treated with high temperature gas. Some of the numerous problems encountered in the previous methods and apparatus will be described hereinafter. For example, in the thermal decomposition process for decomposing petroleum hydrocarbon, the following methods are used in which high temperature gas functions as the heat transfer medium:

1. The heat-exchange method — in which the petroleum hydrocarbon is contacted with a treating gas preheated to a prescribed temperature by use of a heat-exchanger in order to decompose the petroleum hydrocarbon.
2. The partial combustion method — in which the petroleum hydrocarbon is fed into a decomposition chamber together with steam and air such that a portion of the petroleum hydrocarbon is subjected to combustion for heating the remaining portion of the petroleum hydrocarbon and steam whereby the remaining portion is decomposed by the action of superheated steam.

The former method has the disadvantage of necessitating a heat-exchanger, while the latter method has the two drawbacks of trying to maintain the combustion atmosphere in the decomposition furnace always constant and trying to prevent undesirable coke function due to incomplete combustion of the petroleum hydrocarbon.

By way of further example, in the drying or distilling process for solid material, it is necessary to use a high temperature gas as the heat transfer medium which is substantially inert and does not oxidize or burn the solid material. Furthermore, this high temperature gas must always be produced at constant temperature and with uniform composition. However, it has not been possible for the prior art distillation or drying methods and apparatus to completely satisfy such requirements.

Furthermore, as another example, in the oxidizing process of coal or metal ores by means of a high temperature treating gas, it is necessary to accurately control the quantity and temperature of the oxygen or air used as the oxidizing agent, but these requirements have not been completely satisfied with the prior art methods and apparatus in which fuel is burnt after mixing with a large excess of air and the heat energy of the burnt gas is utilized as the heating source with the excess air in the burns gas being used as the oxidizing agent.

For still another example, in the process of reducing metal oxides or metal ores with a high temperature reducing gas, it is necessary to feed a reducing gas, such as carbon monoxide, to the reaction system at a constant temperature and concentration, but in order to prepare such a reducing gas, it has been necessary in the prior art to use a heat-exchanger and such renders the reducing process too expensive. Also, in the activated carbon manufacturing process, the conventional activation of the carbonized material is carried out in either of two techniques — the carbonized material is either treated with a high temperature steam which has been superheated by preheating, or the carbonized material is treated with a mixed high temperature gas produced by the combustion of fuel mixed simultaneously with air and steam so that the mixed gas contains the steam superheated with the combustion heat. However, a special heat-exchanger is required for superheating the steam in one technique whereas in the latter technique, it is difficult to maintain constant the temperature of the mixed gas.

SUMMARY OF THE INVENTION

It is therefore a primary object of this invention to provide a new and improved method for treating raw material with a treating gas which overcomes the foregoing drawbacks and disadvantages associated with the prior art.

It is another object of the present invention to provide an improved method for treating raw material with a treating gas in which the treating conditions can be constantly maintained whereby products having uniform and superior quality can be produced.

It is a further object of the invention to provide an improved method for treating raw material with a treating gas in which the treating operation is simplified and wherein continuous operation is possible.

It is yet another object of the invention to provide an improved method for treating raw material with a treating gas in which thermal efficiency and yield of product are high, operation costs are low, and a heat-exchanger is unnecessary thereby lowering considerably overall equipment cost.

Another object of the invention is to provide an improved method for thermal decomposition of petroleum hydrocarbons in which the thermal decomposition of petroleum hydrocarbon can continuously be carried out under constant conditions yielding products having superior quality with low content of by-products, such as tar or coke, at a high yield rate.

Another object of the invention is to provide an improved method for distilling solid material with an inert high temperature treating gas in which the solid material can be distilled uniformly without oxidation or combustion to obtain products having superior quality at a high yield rate.

Yet another object of the invention is to provide an improved method for oxidizing solid material with a high temperature oxidizing treating gas in which solid material can be oxidized uniformly without burning to obtain products having superior quality at a high yield rate.

Still another object of the invention is to provide an improved method for reducing solid material with high temperature reducing treating gas in which solid material is reduced uniformly to produce products having superior quality at a high yield rate.

A further object of the invention is to provide an improved method for activating carbonized material with a treating gas containing superheated steam in which carbonized materials are activated uniformly to produce products having superior quality at a high yield rate.

Another object of the invention is to provide an improved method and apparatus for altering gaseous raw material with a high temperature treating gas wherein the gaseous raw material, such as natural gas, oil gas and water gas, is converted to another gas having a desired composition at a high yield rate.

A further object of the invention is to provide an improved method for treating another gaseous or solid raw material with a treating gas which is suitably conditioned to a desired temperature and composition and in which the treating operation is easy to carry out, has a low operating cost, and the product is obtained at a high yield rate and has an excellent and uniform quality.

The above and other objects are carried out by an apparatus comprising a mixing chamber having a fuel inlet and air inlet for respectively admitting fuel and air into the mixing chamber wherein they are mixed to produce a combustible mixture. A combustion chamber receives the combustible mixture and burns the same to evolve hot products of combustion which are fed directly into a conditioning chamber. Additional gas is supplied to the conditioning chamber and mixed with the products of combustion to form a suitably conditioned treating gas. To promote rapid and uniform mixing of the gases, the conditioning chamber is connected directly to and has a volume at least 1½ times greater than the combustion chamber. A treating chamber is disposed downstream from the conditioning chamber and receives the preconditioned treating gas and the raw material to be treated.

In accordance with the method of the invention, the treating gas is prepared by mixing the inert products of combustion with an additional gas which is selected in relation to the raw material being treated for carrying out the desired treatment. The temperature and composition of the treating gas is adjusted to a prescribed condition during the mixing operation so that the raw material is treated and processed with a treating gas which has been adjusted to the prescribed treating condition. An important feature of the invention is that the conditioning operation for suitably conditioning the treating gas and the treatment operation of the raw material are carried out separately within separate chambers. This method of treating raw material with such a treating gas was completely unknown prior to the present invention.

Further objects, advantages and features of the present invention will become evident upon a reading of the following description thereof and with reference to the accompanying drawings.

BRIEF DESCRIPTION OF DRAWINGS

FIG. 1A is a schematic cross-sectional side view of one embodiment of a mixing chamber-combustion chamber-conditioning chamber assembly forming part of the apparatus of the present invention;

FIG. 1B is a schematic front view of the assembly shown in FIG. 1A;

FIG. 1C is a schematic top view of the assembly shown in FIG. 1A;

FIG. 2 is a schematic flow sheet of one embodiment of the present invention;

FIG. 3 is a schematic flow sheet of another embodiment of the present invention;

FIG. 4 is a schematic flow sheet of still another embodiment of the present invention;

FIG. 5A is a schematic cross-sectional side view of one embodiment of a mixing chamber-combustion chamber-conditioning chamber-treating chamber assembly forming the apparatus of the present invention;

FIG. 5B is a schematic front view of the assembly shown in FIG. 5A;

Similar reference characters refer to similar parts throughout the several views in the drawings.

DESCRIPTION OF PREFERRED EMBODIMENTS

Figure 6:
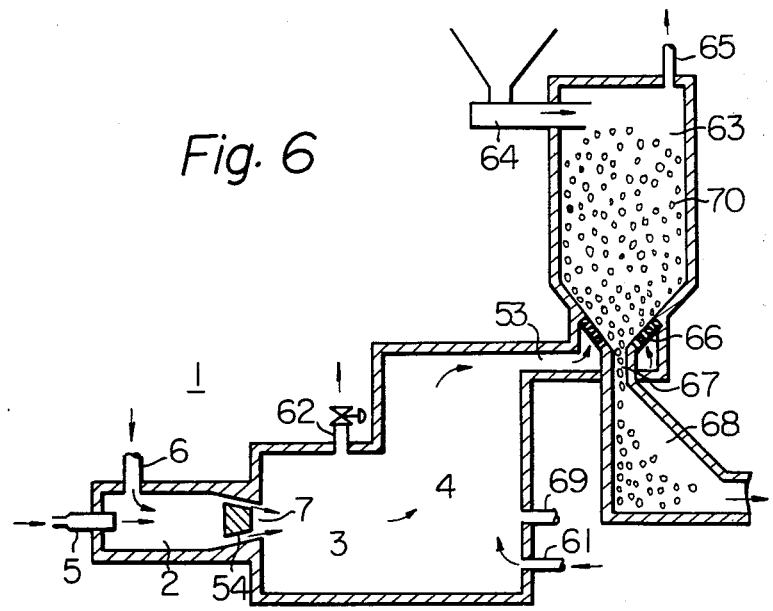
FIG. 6 is a schematic cross-sectional side view of another embodiment of the overall assembly of the present invention.

The method and the apparatus used to carry out the method of the invention will now be described with respect to the embodiment shown in FIGS. 1A-1C which depict a conditioner assembly 1 for preparing and suitably conditioning a treating gas to a prescribed condition at a location upstream of and spaced from the treating chamber for treating the raw material. The assembly 1 is composed of a mixing chamber 2, a combustion chamber 3 and a conditioning chamber 4 all directly interconnected as shown.

The mixing chamber 2 has a cylindrical shape as shown in FIGS. 1A, 1B and 1C. Fuel supply means 5 and oxygen or air supply means 6 are provided at an end portion of the chamber 2 and the fuel and oxygen or air supplied to the mixing chamber 2 are mixed uniformly therein and the resulting mixed fuel gas is ejected into the combustion chamber 3 through an outlet opening 7 formed at the opposite end of the mixing chamber. This mixed fuel gas is ignited and burned within the combustion chamber 3. The combustion chamber 3 has a cylindrical shape as shown in FIGS. 1A, 1B and 1C and is connected to and opens directly into the mixing chamber by way of the outlet opening 7 at one end of the cylindrical combustion chamber 3, while the other end of the combustion chamber 3 opens directly into the conditioning chamber 4. The burnt gases generated within the combustion chamber 3 are introduced into the conditioning chamber 4 and mixed therein with a prescribed amount of additional gas supplied by an additional gas feeding means 8. There is no particular restriction on the general shape of the conditioning chamber 4, however, its relative volume is very important.

In order to make the mixed fuel gas burn completely and stably within the combustion chamber 3 of the assembly 1, it is necessary for the mixed fuel gas which is introduced into the combustion chamber 3 to have sufficient combustion space and the following relation is necessary between the internal diameter $d_M$ of the outlet opening 7 and the internal diameter $d_c$ of the combustion chamber 3:

$$d_c \geq 1\tfrac{1}{4} d_M$$

Also, in order to have complete mixing of the burnt gas and the additional gas in the conditioning chamber 4 and have it adjusted to the prescribed condition, the following relation is necessary between the volume $V_c$ of the combustion chamber 3 and volume $V_A$ of the conditioning chamber 4:

$$V_A \geq 1\tfrac{1}{4} V_c$$

In the event $d_c$ is smaller than $1\tfrac{1}{4} d_M$, combustion of the mixed fuel gas is not completed within the combustion chamber 3 and as a result, incompletely burned combustion gas is introduced into the conditioning chamber 4 and this incomplete burnt gas burns further in the conditioning chamber 4 and/or becomes mixed with the additional gas to form undesirable soot. Also, in the event $V_A$ is smaller than $1\tfrac{1}{4} V_c$, such results in incomplete and nonuniform mixing of the burnt gas and additional gas in the conditioning chamber 4 and as a result, the conditioning of the treating gas becomes nonuniform.

For a better understanding of the present invention, several practical processes will be explained in further detail with reference to FIGS. 2–4.

FIG. 2 is a flow sheet showing a thermal decomposition process of petroleum hydrocarbon. In FIG. 2, fluid fuel such as town gas, oil gas, heavy oil or light oil along with gaseous oxygen or air are introduced into the conditioner assembly 1. The quantity of oxygen gas or air which is introduced with the fuel must be sufficient for complete combustion of the fuel. The conditioner assembly 1 is composed of a mixing chamber 2, combustion chamber 3 and conditioning chamber 4 as described above with reference to FIG. 1. In operation, the fuel and oxygen gas or air are mixed thoroughly in the mixing chamber 2 and the mixed fuel gas is next ejected into combustion chamber 3 where it is ignited and complete combustion takes place. The free oxygen content of the burnt gas generated in the combustion chamber 3 must be below 2% in volume. That is, the amount of oxygen gas or air introduced into the mixing chamber 3 must be sufficient for complete combustion of the fuel, although it is not desirable to have it present in large excess and this excess must be less than 2% with respect to the volume of the burnt gas.

The burnt gas obtained in this manner is a substantially inert gas and is introduced into the conditioning chamber 4 from the combustion chamber 3. Then additional gas in the nature of steam is ejected into the conditioning chamber 4 and mixed uniformly with the products of combustion so as to prepare a suitably conditioned treating gas. The amount of stream to be mixed with the burnt gas is predetermined on the basis of the quantity of burnt gas produced and its temperature so that the resulting mixed gas will have the desired temperature and composition most suitable for decomposing petroleum hydrocarbon. Moreover, the mixed gas which has been conditioned in the conditioner assembly 1 must have a steam content larger than 10% in volume for if the steam content is smaller than 10%, incomplete decomposition of the petroleum hydrocarbon will occur.

The conditioned treating gas is then introduced from the conditioner assembly 1 into a treating chamber 9 along with the raw petroleum hydrocarbon. The materials are thereafter stored within the treating chamber 9 for a prescribed time, during which time the petroleum hydrocarbon in the mixed gas is decomposed by the heat of the burnt gas and action of the steam to thereby manufacture the desired product. The decomposed gas manufactured by such a decomposition reaction is fed to a separator 10 where it is refined by removing therefrom by-products such as pitch and tar. The purified decomposed gas is then sent to a holder 11 where it is stored and used as desired. A part of the decomposed gas which is stored in the holder 11 can be recycled and used as fued gas. The by-products, such as pitch and tar, which are separated by the separator 10 are sent to a preheating gas generator where they are burned and the resultant burnt gas is thereafter used for preheating the fuel, air or oxygen gas, or the steam and petroleum hydrocarbon to the prescribed temperature.

An important feature of the present invention is that burnt gas and steam are mixed, independently of the petroleum hydrocarbon, to prepare a treating gas having the prescribed temperature and composition and the treating gas is then mixed with petroleum hydrocarbon thereby adjusting the temperature and composition of the decomposition system to the desired condition. Namely, the parameters for controlling the decomposition are adjusted within the conditioner assembly 1 during preparation of the treating gas and the decomposition of the reaction system whose reaction condition has been adjusted is thereafter carried out separately within the treating chamber 9. That is, the conditioning operation of forming the treating gas from burnt gas and steam and the thermal decomposition operation of decomposing petroleum hydrocarbon by means of burnt gas and steam are carried out in separate chambers, and this is an entirely new technique which has not been attempted in the past.

In the prior art systems in which burnt gas has been used as the heat transfer medium, it was difficult to constantly maintain the temperature of the decomposition system and consequently, the composition of the decomposed gas has typically been nonuniform; such a drawback has been completely overcome by the method of the present invention. In the general decomposition of petroleum hydrocarbon, a catalyst is not required nor is a heat transfer solid required, thus, preparation and replacement of the catalyst and heating of the heat transfer solid are not necessary so that continuous operation is possible. However, in the case of certain specified decompositions, it is preferable to use a catalyst and such can be added in the treating chamber 9 for accelerating the decomposition rate.

There is no particular restriction on the petroleum hydrocarbon to which the method of this invention can be applied and straight gasoline, naphtha, light oil, kerosene oil, heavy oil, crude oil and distilled tar can be used effectively. The content of free oxygen in the treating gas to be mixed with the petroleum hydrocarbon must be controlled to below 2%, preferably below 0.5%, so as to prevent undesirable oxidizing decomposition of the petroleum hydrocarbon.

As explained above, the treating method of the invention can be applied for the conversion of natural gas and for oxidation of aliphatic or aromatic hydrocarbons such as paraffins, benzene, naphthalene, xylenes, etc. However, in the case of conversion of natural gas, steam is used as the additional gas and a suitable catalyst is contained in the treating chamber. Also, in the oxidation of the aforementioned hydrocarbons, these hydrocarbons are fed to the treating chamber in the vapor phase, and air or oxygen gas is used as the additional oxidizing gas and a suitable catalyst such as vanadium pentoxide ($V_2O_5$) is present in the treating chamber.

As another example, the distillation process of solid materials will now be explained with reference to FIG. 3. Fuel and oxygen gas or air are introduced into the mixing chamber 2 of the conditioner assembly 1 and mixed and the mixed fuel gas is ejected into the combustion chamber 3 and burned therein. The burnt gas is introduced into the conditioning chamber 4. The free oxygen gas content of the burnt gas must be maintained below 2%, preferably below 0.5%, for if the free oxygen gas content exceeds 2%, the solid material to be treated will be oxidized or burnt by this free oxygen hence lowering the quality and yield of the product.

Inert gas, such as nitrogen gas or carbon dioxide gas, is introduced into the conditioning chamber 4 as the additional gas in order to adjust the temperature and composition of the burnt gas so as to prepare the treating gas. A part of the burnt gas may be withdrawn from the combustion chamber 3 and stored in the storage means 22 and this withdrawn gas can be sent to the conditioning chamber as additional inert gas, as required. The treating gas whose temperature and composition have been suitably conditioned in this manner is fed to a treating chamber 21. Solid material to be distilled, such as coal, lignite, peat and wood, are charged into the treating chamber 21 and distilled therein by the treating gas.

There is practically no oxidation or combustion of the solid material during the distillation because the treating gas is practically an inert gas. Also, products of uniform quality can be obtained because the treating gas always has a constant temperature and composition and therefore the resultant products are better than previous products. The distilled gas produced by distillation in the treating chamber 21 can be recycled and used as fuel. Also, a portion of this distilled gas can be sent to the preheating gas generation 23 where it is burned and thereafter the burnt gas is sent to fuel preheating means 13, an oxygen gas or air preheating means 14 and an additional gas preheating means 24 to preheat the fuel, oxygen on air, and additional gas to their respective prescribed temperatures. The conditioning of the treating gas can be carried out more accurately and precisely by such preheating.

As a further example, the oxidation process of solid materials will now be described with reference to FIG. 4. Fuel and air or oxygen gas are supplied to the mixing chamber 2 of the conditioner assembly 1 and mixed therewithin. The gas mixture is ejected into the combustion chamber 3 and burned therein and the burnt gas produced in this manner is introduced into the conditioning chamber 4. At this time, a prescribed quantity of additional gas in the form of oxygen gas or air is introduced into the conditioning chamber 4 and mixed with the burnt gas to thereby form the oxidation treating gas having a suitable temperature and oxygen content. The treating gas is then introduced into an oxidation chamber 31 in which coal or metal ore to be oxidized has been charged. In the above operation, it is necessary to maintain the free oxygen content of the burnt gas produced in the combustion chamber 3 below 2%, and preferably below 0.5%, so as to sufficiently control the free oxygen content in the treating gas and prevent large fluctuation of the quality of oxidized product.

In case the quantity of burnt gas produced within the combustion chamber 3 is larger than the desired quantity, the excess is withdrawn from the combustion chamber and stored in the storage means 22, and may be recycled to the conditioning chamber as required. Also, the temperature of the fuel, air or oxygen gas introduced into the mixing chamber and the temperature of the oxygen gas or air fed as additional gas to the conditioning chamber can be controlled to the prescribed temperature by suitable temperature control means 13, 14 and 33 which make it possible to control the temperature of the treating gas more accurately and precisely than would otherwise be the case.

The treating process just described with reference to FIG. 4 is also suitable process for the reduction of metal ores and metal oxides. In this case, a reducing gas such as carbon monoxide gas is used as the additional gas. Also, it is necessary to make the free oxygen content in the burnt gas precisely below 2%, preferably below 0.5%, in order to prevent wasteful consumption of the reducing gas.

The treating process shown by the flow sheet in FIG. 4 is also suitable for the activation of carbonized material. The additional gas in this case is steam and it is necessary to maintain the free oxygen content in the burnt gas below 2%, preferably below 0.5%, in order to prevent loss of the carbonized material.

Next, an example of petroleum hydrocarbon decomposition will be delineated with reference to the apparatus shown in FIGS. 5A-5B. In FIGS. 5A and 5B, the mixing chamber 2 of the conditioner assembly 1 has a cylindrical inner space, and the fuel inlet 5 and oxygen gas or air inlet 6 are provided at one end thereof. The inner wall located at the other end of the mixing of the mixing chamber 2 is conical and narrows toward and terminates in the gas outlet opening 7 formed at its end. Due to the flow restriction defined by the converging wall section, the mixed fuel gas in the mixing chamber 2 is ejected therefrom at high velocity and with great force into the combustion chamber 3 through the gas ejecting end portion. Uniform diffusion of the mixed fuel gas into the combustion chamber 3 can be obtained by providing gas ejecting control means at the gas ejecting end portion 55.

An embodiment of the gas ejecting control means is shown in FIG. 5A and such comprises a movable control member 54 having a concial outer surface parallel with respect to the conical inside surface of the converging wall section of the gas ejecting end portion 55. The position of the conical member 54 can be selectively changed in the directions shown by the arrow $a$ in FIG. 5A. The clearance between the conical surface of the conical control member 54 and the conical inside portion of the gas ejecting end portion 55 can be carefully controlled by changing the position of the conical control member 54 to thereby control the ejecting speed and ejecting direction of the mixed fuel gas.

The conical control member 54 has a truncated narrow end portion which faces the combustion chamber 3 and hence is exposed to the high temperature conditions prevailing therein. The conical taper of the control member performs a throttling function and the truncation of the narrow end of the control member effectively minimizes overheating of the control member since only a minimum portion thereof projects into the combustion chamber where the high combustion temperatures prevail. By such a structure, the gas ejecting control means assists in accurately controlling the parameters of the treating gas by controlling the fuel mixture feed rate into combustion chamber.

The combustion chamber 3 has a horizontal cylindrical combustion space and the downstream end thereof is completely open and communicates directly with a circular inlet opening in the conditioning chamber 4. An additional gas inlet 8 is provided at the base of the chamber 4 and though location thereof is not particularly limited, it has been found that uniform and fast mixing of burnt gas and additional gas can be carried out by making the feeding direction of additional gas counter-current to the introducing direction of burnt gas from the combustion chamber 3. In the present example of decomposing petroleum hydrocarbon, the additional gas comprises steam as described with reference to FIG. 2.

A treating chamber 9 is attached to the conditioning chamber 4 and a petroleum hydrocarbon inlet 51 is provided for charging petroleum hydrocarbon into the treating chamber to mix with and be processed by the treating gas. A discharge outlet 52 provides communication between the outlet end portion of the conditioning chamber 4 and the treating chamber 9 for supplying the conditioned treating gas to the decomposition chamber 9. The decomposed gas produced by decomposition in the decomposition chamber 9 is discharged from the decomposition chamber 9 by way of the exhaust 53. An important feature of the invention resides in the particular location of the raw material inlet 51. As seen in FIGS. 5A and 5B, the inlet 51 is connected to the treating chamber 9 at the base thereof in proximity to the outlet 52 so as to feed the raw material into the treating chamber 9 at a location adjacent to where the treating gas is fed through the outlet 52 thereby promoting thorough intermixing and dispersing of the treating gas and raw material. This arrangement is particularly useful for treating liquid and gaseous raw materials.

Another embodiment of apparatus is hereinafter explained with reference to FIG. 6 for distilling solid material. The mixing chamber 2 of the conditioner assembly 1 is approximately the same as the mixing chamber 2 shown in FIG. 5 and extends horizontally. The combustion chamber 3 also extends in a horizontal direction and has an exhaust outlet 62 for withdrawing a portion of the burnt gas.

The conditioning chamber 4 is provided with an inert gas inlet 61 for introducing an inert gas such as nitrogen gas or carbon dioxide gas, and burnt gas inlet 69 is connected through a conduit (not shown) to the gas exhaust outlet 62.

A treating chamber comprising a distillation chamber 63 is provided with a feeder device 64 at an upper portion thereof for feeding the solid material 70 which is to be distilled. The distillation chamber 63 has a discharge outlet 67 at the center of its bottom, slanted in a funnel shape and which connects with a cooling chamber 68. The slanted side of the bottom portion is provided with a plurality of apertures 66 through which the conditioned treating gas from the conditioning chamber 4 is introduced into the distillation chamber. The treating gas passes through the solid material layer and is discharged from the chamber 63 through an exhaust outlet 65. The desired distillation is carried out by heating the solid material while the treating gas is passing through the solid material layer.

The apparatus shown in FIG. 6 can also be utilized for the oxidation process of solid material such as coal or metal ores. The apparatus of FIG. 6 is applicable further to the reduction process of oxidized materials.

Next, another embodiment of apparatus for the activation of carbonized material will be explained with reference to FIG. 7. The mixing chamber 2 of the conditioner assembly 1 extends vertically and ejects the mixed fuel gas downward into the combusion chamber 3 through the gas ejecting opening 7. The combustion chamber 3 has a cylindrical shape and extends in the vertical direction. The combustion chamber 3 is provided with withdrawing means 62 for withdrawing excess burnt gas in the combustion chamber 3 and the conditioning chamber 4 is provided with a steam feeding means 8. In the example shown in the drawing, two steam inlets 8a and 8b are provided. The conditioning chamber 4 is also provided with an inlet 69 for feeding, as required, burnt gas which has been withdrawn from the combustion chamber 3.

The treating chamber comprises an activating chamber 71 for activating carbonized material and a raw material feeder device 74 is disposed at its lower portion for feeding carbonized material 75 which is to be activated. The lower portion of the activating chamber 71 is formed in a funnel shape with a partition 73 at its lower ends. The partition has a plurality of apertures and the treating gas is introduced upwardly into the activating chamber 1 by flowing through passage 53 and through the apertures to activate and carbonized material and form therewith a fluidized bed. The activated material 76 is blown up by the flow of the treating gas and is discharged through an exhaust outlet 72.

The method and apparatus of the present invention will be explained in further detail with reference to the following examples.

EXAMPLE 1

The present example pertains to the manufacturing of town gas for fuel from light naphtha as the raw material. For this purpose, the decomposition apparatus of the type shown in FIG. 5 was used. The inner volume $V_c$ and $V_a$ of the combustion chamber and conditioning chamber of the conditioner assembly was 0.1 m³ and 0.4 m³, respectively, and the internal diameter $d_M$ of the outlet opening of the mixing chamber and the internal diameter $d_c$ of the combustion chamber was 4 cm. and 30 cm., respectively. Therefore, the relations beween $d_M$ and $d_c$, and $V_A$ and $V_c$ are:

$d_c = 7.5 d_M$ and $V_A = 4V_c$.

Kerosene and air were introduced into the mixing chamber at flow rates of 10 liter/hr. and 120 m³/hr., respectively, and these were successively subjected to the steps of mixing with each other within the mixing chamber, ejecting into the combustion chamber and igniting and burning within the combustion chamber. The burnt gas prepared in this manner was introduced into the conditioning chamber, and mixed with steam introduced individually into the conditioning chamber whereby a desired treating gas was prepared from the burnt gas and the steam. Light naphtha to be decomposed was then mixed with this treating gas in the treating chamber and the temperature of the mixed treating gas was adjusted to 850° C. The steam was introduced at a flow rate of 400 kg/hr. and the light naphtha at 350 kg/hr. This mixed gas containing naphtha was introduced into a decomposition chamber having a volume of 3m³ to decompose the light naphtha. After decomposition of the light naphtha was started in this manner, a portion of the decomposed gas was recycled and used as fuel which was fed to the mixing chamber. When the operation had reached the normal condition, the free oxygen content in the burnt gas was 1.3% and the steam content in the mixed gas containing the light naphtha was 25.3%. Also, the pressure in the decomposition chamber was 0.5% kg/cm². The composition and calorific value of the decomposed gas obtained by this example was as shown in Table 1.

Table 1

| | Component | Content (% by volume) |
|---|---|---|
| | $CO_2$ | 3 |
| | $C_2H_4$ | 24 |
| | $C_2H_6$ | 6 |
| Composition of | $O_2$ | 1 |
| decomposed gas | CO | 4 |
| | $H_2$ | 25 |
| | $CH_4$ | 14 |
| | $N_2$ | 23 |
| Calorific value of decomposed gas | | 7200 Kcal/m³ |
| Total gasification efficiency | | 92% |

The decomposition gas obtained in this example was a fuel gas with a high calorific value of 7200 Kcal/m³, and was an ideal town gas as the carbon monoxide content was relatively low and the hydrogen content was relatively high.

EXAMPLE 2

The present example is concerned with the manufacturing of ethylene from light naphtha as the raw material. The decomposition apparatus of the type shown in FIG. 5 was used for this manufacture, in which the inner volume $V_c$ and $V_A$ of the combustion chamber and conditioning chamber was 0.2 m³ and 0.6 m³, respectively, and the inside diameter $d_M$ of the outlet opening and the diameter $d_c$ of the combustion chamber was 7 cm. and 45 cm., respectively. Therefore the relations between $d_M$ and $d_c$, and $V_c$ and $V_A$ are: $d_c = 6.4 d_M$ and $V_A = 3V_c$.

Kerosene and air were introduced into the mixing chamber at flow rates of 10 liter/hr. and 120 m³/hr., respectively, and these were mixed within the mixing chamber, sent into the combustion chamber, and ignited and burned within the combustion chamber. Next, steam was introduced at a flow rate of 350 kg/hr. into the conditioning chamber to prepare a mixed gas of 880° C. This mixed gas was introduced immediately into a decomposition chamber having an inner volume 3.5 m³ to decompose the light naphtha which was introduced therein at 350 kg/hr.

After decomposition of the naphtha had been started in this manner, a portion of the light naphtha decomposed gas was recycled and used as fuel which was fed to the mixing chamber. When the operation had reached the normal condition, the free oxygen content in the burnt gas was 0.7% and the steam content in the mixed gas was 23%. Also, the pressure in the decomposition furnace was 0.5 kg/cm². The composition of the decomposed gas obtained by the present example was as shown in Table 2, from which can be seen that the ethylene conversion rate was excellent.

Table 2

| | Component | Content (% by volume) |
|---|---|---|
| Composition of | $C_2H_4$ | 30 |
| decomposed gas | $C_2H_6$ | 7 |
| | $CH_4$ | 25 |
| Ethylene conversion rate | | 40% |

The ethylene conversion rate is defined as the precent by weight of ethylene obtained on the basis of the weight of raw petroleum hydrocarbon.

EXAMPLE 3

The present example is concerned with the manufacturing of town gas from kerosene as the raw material. The decomposition apparatus of the type shown in FIG. 5 was used for this purpose. The inner volume $V_c$ and $V_A$ of the combustion chamber and the conditioning chamber, and the inside diameter $d_M$ of the outlet opening of the mixing chamber and the diameter $d_c$ of the combustion chamber was 0.12 m³ and 0.45 m³, and 4.6 cm. and 33 cm. respectively. Consequently, the relations between $d_M$ and $d_c$, and $V_A$ and $V_c$ are: $d_c = 7.2 d_M$ and $V_A = 3.7 V_c$.

Kerosene preheated to 250° C. and air preheated to 300° C. were introduced into the mixing chamber at flow rates of 10 liter/hr. and 120 m³/hr., respectively. The kerosene was burned in the same manner as in Example 1. Steam preheated to 600° C. was introduced into the conditioning chamber at a flow rate of 240 kg/hr. to mix with the burnt gas containing the burnt gas and steam.

This mixed gas was introduced immediately into the decomposition chamber having an inner volume 3.2 m³ to carry out decomposition of the kerosene which was fed thereto at 400° C. at 150 kg/hr.

After decomposition of kerosene had been started in this manner, a portion of the kerosene decomposed gas was recycled and used as fuel which was fed to the mixing chamber. When the operation had reached the normal condition, the free oxygen content in the burnt gas was 0.8% and the steam content in the mixed gas was 34.7%. Also, the pressure in the decomposition chamber was 0.6 kg/cm². The composition of the decomposed gas obtained by the present example was as shown in Table 3.

Table 3

| | Component | Content (% by volume) |
|---|---|---|
| | $CO_2$ | 3 |
| | $C_2H_4$ | 25 |
| | $C_2H_6$ | 5 |
| Composition of | $O_2$ | trace |
| decomposed gas | CO | 3 |
| | $H_2$ | 23 |
| | $CH_4$ | 16 |
| | $N_2$ | 25 |
| Calorific value | | 7250 Kcal/m³ |
| Total gasification efficiency | | 92.5% |

The decomposed gas of the present example is an ideal town gas as the calorific value is very high, carbon monoxide content is low and hydrogen content is high, as is clear from Table 3.

EXAMPLE 4

The present example is concerned with the manufacturing of synthetic gas from light naphtha as the raw material. The same conditioner assembly as used in Example 3 was used for the present example.

Town gas and air were introduced into the mixing chamber at flow rates of 15 m³/hr. and 80 m³/hr., respectively, the mixed fuel gas was burned in the combustion chamber steam and was mixed with the burnt gas within the conditioning chamber to prepare a mixed gas of 900° C. The flow rate of the steam was 460 kg./hr.

The mixed gas was introduced immediately into the decomposition chamber having an inner volume 3.2 m³. A nickel catalyst was charged on the checker bricks in the decomposition chamber and light naphtha was charged therein at 350 kg/hr.

When the operation had reached the normal condition, the free oxygen content in the burnt gas was 0.4%, the steam content in the mixed gas was 41% and the pressure in the decomposition chamber was 11 kg/cm². The composition of the decomposed gas obtained by the present example was as shown in Table 4. It was possible to manufacture synthetic gas with a very good yield rate.

Table 4

| | Component | Content (% by volume) |
|---|---|---|
| Composition of decomposed gas | CO | 18 |
| | $H_2$ | 53 |

EXAMPLE 5

The present example concerns distillation of coal. The advantages and shortcomings of the previous distillation method have already been explained above and the advantages of the method of this invention will be explained while being compared with the previous method (Comparison Example 1) which utilizes burnt gas. The conditioner assembly of the type indicated in FIG. 6 was used for carrying out the present example. The volumes $V_c$ and $V_A$ of the combustion chamber and the conditioning chamber was 0.1 m³ and 0.6 m³, respectively, and $d_M$ and $d_c$ were 0.04 m. and 0.36 m., respectively. Consequently, the following relations existed: $d_c = 9d_M$ and $V_A = 6V_c$.

Distillation gas was used as the fuel and its feed flow rate was 350 m³/hr., while that of the air was 245 m³/hr. These were introduced into the mixing chamber and mixed therewithin, introduced into the combustion chamber, and ignited and burned therewithin. The free oxygen content of the burnt gas was 0.8%. The entire quantity of this burnt gas was introduced into the conditioning chamber and nitrogen gas which had been preheated to 60° C. was also introduced into the conditioning chamber at a feed rate of 1 m³/kg. of coal to prepare a suitably conditioned treating gas of 500° C. The treating gas was introduced into the treating chamber at a feed rate of 7 m³/kg. of coal. Distillation was applied to the coal which had been charged into the treating chamber for 45 minutes and then withdrawn from the furnace. The distilled coke was obtained with a yield of 82%.

On the other hand, in Comparison Example 1, fuel and air were introducecd into the burnt gas chamber of the previous distillation apparatus with the same charging quantity as in the present example and burned immediately. The comparison burnt gas was introduced immediately into the treating chamber. The operating condition of the treating chamber was the same as that of the present example and the treating temperature was 500° C. The burnt gas was introduced at a rate of 7 m³/hr., and the distillation time was 45 minutes. The yield of the comparison coke was 76%, which was much smaller than that of the present example.

In the method of the present example the fuel had burnt completely and the free oxygen content in the burnt gas was very low, whereby good distillation of the coal was carried out in the treating chamber at a high yield and without burning.

EXAMPLE 6

The present example concerns oxidation of bituminous coal. In the manufacturing of organic nitrogenous fertilizer from peat or lignite as the raw material, the method of oxidizing the raw material at a high temperature to increase the acidic component such as humic acid in the raw material, and then reacting the oxidized raw material with ammonia is well-known. The quantity of ammonia absorbed is increased by the oxidation pretreatment and fertilizer having high nitrogen content can be obtained. In this oxidizing case, the temperature and free oxygen content of the oxidizing system must be maintained in a condition such that the raw material is gradually oxidized but does not burn when the raw material is brought into contact with the oxygen. A conditioner assembly of the type indicated in FIG. 6 was used for carrying out the present example. The volumes $V_c$ and $V_A$ of the combustion chamber and the conditioning chamber were 0.15 m³ and 0.6 m³, respectively, $d_M$ and $d_c$ were 0.03 m. and 0.15 m., respectively, therefore, $d_M$ and $d_c$, and $V_c$ and $V_A$ have the following relations: $d_c = 5d_M$ and $V_A = 4V_c$.

Town gas was introduced into the mixing chamber as fuel at a flow rate of 10 m³/hr., and air at 47 m³/hr., and these were burned in the combustion chamber to manufacture inert burned gas with a free oxygen content of 0.4%. This burnt gas was introduced into the conditioning chamber and air whose temperature had been adjusted to 20° C. was introduced into the conditioning chamber at a feed rate of 320 m³/kg. of bituminous coal to prepare oxidation treating gas of 92° C. Also, bituminous coal with a humic acid content of 30% by weight and a particle size of 80 mesh was charged into the treating chamber and the above-mentioned oxidation treating gas was introduced into therein at a feed rate of 380 m³/kg. of bituminous coal.

The treating time for the bituminous coal was 45 minutes and the humic acid content of the oxidized bituminous coal was 57% by weight. Also, there was entirely no trace of burning on the surface of the oxidized bituminous coal. The humic acid content of oxidized bituminous coal produced by the previous method was generally about 40 − 45% by weight and usually some trace of burning was observed on its surface. It was shown that the oxidized bituminous coal obtained by the method of the present example had very superior quality when compared with the previous oxidized one.

EXAMPLE 7

The present example concerns an oxidation pretreatment of raw material coking coal which is carried out for controlling the coking property of the raw coal.

When solid raw material such as coking coal is oxidized with air, the oxidation reaction progresses gradually from the surface of the solid material to the interior. In case the oxidizing agent is a gaseous material such as oxygen or air, there exists the problem that the solid material is burnt within the oxidizing gas if the temperature of the oxidizing gas exceeds a certain critical value, and the yield of an oxidized product is lowered undesirably.

The relation between the amount X of oxygen absorbed by the coal during the oxidation reaction and the reaction time $t$ at a fixed temperature can be expressed by the following equation:

$$X = Ct^b$$

where C is a constant whose value depends upon the kind of coal, and $b$ is a constant whose value depends upon the particle size of the coal.

Consequently, the absorbed quantity X of oxygen increases with longer the reaction times $t$ for a certain kind of coal of a fixed particle size. However, the oxidation temperature must be accurately controlled below the critical value at which combustion takes place.

In the present example, bituminous coal with 12.7% oxygen content (value obtained from elementary analysis) and of 8 mesh was charged into an oxidizing chamber and subjected to an oxidation treatment.

Apparatus of the type indicated in FIG. 6 was used as the conditioner assembly for the present example. The volumes $V_c$ and $V_A$ of the combustion chamber and the conditioning chamber were 0.2 m³ and 0.9 m³, respectively, $d_M$ was 0.03 m. and $d_c$ was 0.15 m. so that the following relations existed: $d_c = 5d_M$ and $V_A = 4.5V_c$.

Town gas was introduced into the mixing chamber at a flow rate of 30 m³/hr. as fuel, and air was introduced at a flow rate of 140 m³/hr. The mixed fuel gas was burned within the combustion chamber and the free oxygen content in the burnt gas was 0.7%. Next, the burnt gas was introduced into the conditioning chamber and air was introduced at a feed rate of 320 m³/kg. of bituminous coal into the conditioning chamber to form the treating gas. The treating gas containing air was introduced into the treating chamber at a feed rate of 370 m³/kg. of bituminous coal.

The bituminous coal was treated for 10 hours in the treating chamber with the treating gas by which oxidized bituminous coal with 19.5% oxygen content was manufactured.

The oxygen content of the oxidized bituminous coal oxidized by the previous method from the same bituminous coal was about 14 – 15%. Consequently, it can be appreciated that the oxidized bituminous coal manufactured by the present example had a very high oxygen content.

EXAMPLE 8

Ore containing metal oxide is normally reduced to prepare the crude metal. The present example concerns a method of manufacturing crude tin by reducing tin ore by means of a high temperature reducing gas.

Carbon monoxide gas is used as the reducing gas in the reduction process of tin ore and generally, such is carried out at a temperature of about 900° C. The chemical reaction is as indicated by the following chemical equation:

$$SnO_2 + 2CO = Sn + 2CO_2$$

When the reducing temperature for the tin ore becomes higher than 900° C., particularly above 1200° C., loss of tin results due to vaporization. Therefore it is necessary to precisely control the temperature to the prescribed value.

The same type apparatus as that shown in FIG. 1 was used for the present example. The volumes $V_c$ and $V_A$ of the combustion chamber and the conditioning chamber were 0.2 m³ and 0.9 m³, respectively, and $d_M$ and $d_c$ were 0.03 m. and 0.15 m., respectively. Consequently, the following relations existed: $d_c = 5d_M$ and $V_A = 4.5V_c$.

Town gas was introduced into the mixing chamber at a flow rate of 40 m³/hr. as fuel, and air was introduced at a flow rate of 170 m³/hr. The mixed fuel gas was introduced into the combustion chamber and ignited and burned completely in the combustion chamber. The free oxygen content in the burnt gas was 0.5%. Next, the burnt gas was introduced into the conditioning chamber. Carbon monoxide gas was introduced from a carbon monoxide producer into the conditioning chamber at a feed rate of 4 m³/kg. of tin ore. The carbon monoxide was mixed with the burnt gas to prepare a reduction treating gas of 870° C.

Tin ore with a tin content of 62% was then charged into the reducing chamber. The reduction treating gas was introduced into this reducing chamber at a feed rate of 67 m³/kg. of tin ore. Reduction of the tin ore was carried out for 40 minutes. The tin content of the crude tin reduced was 84%. As the tin content by the previous method was 75 – 77% from the same tin ore, it was clear that the tin content was very high when compared with crude tin obtained by the previous method.

EXAMPLE 9

The present example concerns an oxidizing process for manufacturing phthalic anhydride from naphthaline.

Apparatus of the type shown in FIGS. 5A and 5B was used for the oxidizing. The volumes $V_c$ and $V_A$ of the combustion chamber and the conditioning chamber of the conditioner assembly were 0.1 m³ and 0.4 m³, respectively. The inside diameters $d_M$ and $d_c$ of the outlet opening and the combustion chamber were 0.04 m. and 0.32 m., respectively. Consequently, the following relations were obtained. $d_c = 8 d_M$ and $V_A = 4V_c$.

Town gas and air were introduced into the mixing chamber at flow rates of 5 m³/hr. and 24 m³/hr., respectively, and mixed within the mixing chamber. The mixed fuel gas was introduced into the combustion chamber and burned therewithin and the free oxygen content of the burnt gas was 0.2%. The burnt gas was introduced into the conditioning chamber and mixed with air which had been introduced into the conditioning chamber to prepare the treating gas.

Next, vaporized naphthalene which had been heated to a temperature of 200° C. was introduced into the treating chamber and mixed therewithin with the treating gas to prepare a mixed gas of 380° C. containing naphthalene. The air was introduced into the conditioning chamber at a feed rate of 28 m³/kg. of naphthalene and the feed rate of the vaporized naphthalene into the treating chamber was 1 kg. naphthalene/30 m³ of treating gas. In order to promote oxidation, vanadium pentoxide ($V_2O_5$) was charged into the treating chamber.

The yield of the phthalic anhydride obtained by the oxidizing was 90%.

EXAMPLE 10

The present example concerns a conversion process of natural gas. The same apparatus as that used in Example 4 was used for the present example. Natural gas as fuel along with air were introduced at flow rates of 42 m³/hr. and 79 m³/hr., respectively, into and mixed in the mixing chamber. The mixed fuel gas was introduced into the combustion chamber and burned therewithin and the free oxygen content of the burnt gas produced in this manner was 0.2%. The burnt gas was introduced into the conditioning chamber and mixed with steam which was introduced into this conditioning chamber at a feed rate of 30 kg/hr. to prepare the treating gas.

The suitably conditioned treating gas was introduced into a conversion chamber containing a nickel catalyst and natural gas was fed into the treating chamber at a feed rate of 100 m³/hr. and subjected to a conversion treatment. The compositions of the natural gas used as raw material and the converted gas are shown in Table 5, from which it can be seen that it has a preferable hydrogen content.

Table 5

| Component | Content (% by volume) | |
|---|---|---|
| | Natural Gas | Converted Gas |
| $CH_4$ | 93 | 10 |
| $CO_2$ | 4 | 2 |
| $H_2$ | — | 43 |
| $CO$ | — | 19 |
| $N_2$ | 3 | 26 |

EXAMPLE 11

The present example concerns an activation process of carbonized material.

Activated carbon can be obtained by contacting carbonized material with an activation gas such as steam for a specified time at a temperature of 700° C. to 1000° C. High quality activated carbon is defined as an activated carbon which has uniform and high activity on its surface and interior. In order to obtain such high quality activated carbon, activation must be carried out under a mild condition so that activation progresses uniformly on the surface and in the interior.

Figure 7:
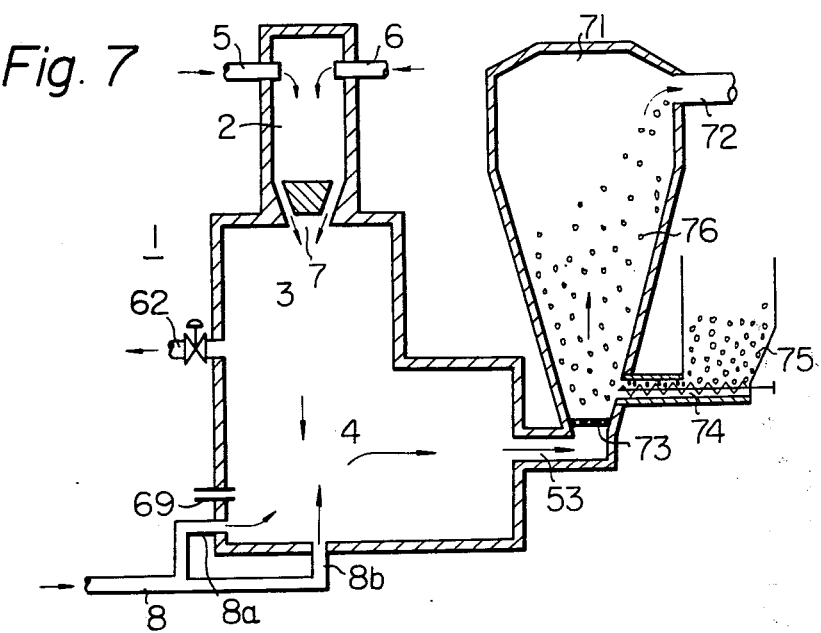
FIG. 7 is a schematic cross-sectional side view of still another embodiment of the overall assembly of the present invention.

In the present example, apparatus of the type shown in FIG. 7 was used. The volumes $V_c$ and $V_A$ of the combustion chamber and the conditioning chamber of the conditioner assembly was 0.1 m³ and 0.4 m³, respectively, and the inside diameters of the outlet opening and combustion chamber were 0.04 m. and 0.3, respectively. Consequently, the relations between $d_M$ and $d_c$, and $V_c$ and $V_A$ are: $d_c = 7.5 d_M$ and $V_A = 4V_c$.

Town gas and air were introduced into the mixing chamber at flow rates of 16 m³/hr. and 90 m³/hr., respectively, and mixed therein and the mixed fuel gas was then introduced into the combustion chamber and burned within the combustion chamber. The free oxygen content of the burnt gas thus obtained was 0.45. The burnt gas was then introduced into the conditioning chamber. Superheated steam of 200° C. was introduced into the conditioning chamber and mixed with the burnt gas to prepare a suitably conditioned treating gas of 950° C. The steam content of the treating gas was 12%. Next, the treating gas was introduced into the treating chamber comprising an activating chamber in which carbonized material had been charged. The carbonized material was activated while floating in the activating chamber in contact with the treating gas.

The activated carbon was a superior product with the interior and surface activated uniformly.

While preferred embodiments of the invention have been described, it is understood that obvious modifications and changes thereto will be apparent to those skilled in the art and the present invention is intended to cover all such obvious modifications and changes which fall within the spirit and scope of the invention as defined in the appended claims.

What I claim is:

1. A method for treating raw material with a treating gas comprising the successive steps of:
    a. mixing, in a mixing chamber, liquid or gaseous fuel and air or oxygen gas in sufficient quantities to obtain complete combustion of said fuel;
    b. ejecting the mixed fuel gas from said mixing chamber into a combustion chamber;
    c. completely burning said mixed fuel gas within said combustion chamber to generate a substantially inert burnt gas containing less than 2% by volume of free oxygen gas;
    d. introducing said burnt gas from said combustion chamber directly into a conditioning chamber having an inner volume of at least 1½ times that of said combustion chamber without passing said burnt gas through any flow restriction;
    e. introducing at least one additional gas selected from the group consisting of steam, reducing gas, oxidizing gas or inert gas at a specified flow rate into said conditioning chamber simultaneously with the introducing of burnt gas thereinto and uniformly mixing the additional gas with said burnt gas to prepare a uniform treating gas having a desired uniform temperature determined solely by the temperatures of said additional and burnt gases without employing any other heating medium and a desired uniform composition;
    f. introducing said treating gas from said conditioning chamber into a treating chamber separated from said conditioning chamber; and
    g. treating a raw material selected from the group consisting of hydrocarbonaceous materials, carbonous materials, metal ores or metal oxides with said treating gas in said treating chamber to obtain a treated raw material product of uniform quality.

2. A method according to claim 1 including introducing at a specified flow rate the raw material into said treating chamber at a location proximate that where said treating gas enters said treating chamber, said flow rate of said raw material being adequate for preparing a uniformly mixed gas containing said raw material and said treating gas.

3. A method according to claim 1 wherein said additional gas is a substantially inert gas whose temperature is controlled so as to control the temperature of said treating gas.

4. A method according to claim 13 wherein said inert gas comprises a portion of said burnt gas which has been withdrawn from said combustion chamber and adjusted to a desired temperature.

5. A method according to claim 1 wherein said additional gas is an oxidizing gas for oxidizing said raw material.

6. A method according to claim 1 wherein said additional gas is a reducing gas for reducing said raw material.

7. A method according to claim 1 wherein said raw material is a carbonized material and said additional gas is steam for activating said carbonized material.

8. A method according to claim 2 wherein said raw material is a petroleum hydrocarbon, and said additional gas is steam having a content larger than 10% by volume with respect to the volume of said mixed gas containing said petroleum hydrocarbon thereby effecting decomposition of said petroleum hydrocarbon by said treating gas containing said steam.

9. A method according to claim 2 wherein said raw material is a hydrocarbon selected from aliphatic and aromatic hydrocarbons, and said additional gas is an oxidizing gas selected from oxygen gas and air thereby effecting oxidation of said hydrocarbon by said treating gas containing said oxidizing gas.

10. A method according to claim 2 wherein said raw material is a gaseous material and said additional gas is steam thereby effecting conversion of said gaseous material by said treating gas containing said steam.

11. A method according to claim 1 wherein at least one of said fuel, oxygen gas and air, and additional gas is pre-adjusted to a temperature prescribed for each thereof prior to said mixing.

12. A method according to claim 2 wherein at least one of said fuel, oxygen gas or air, additional gas and raw material is pre-adjusted to a temperature prescribed for each thereof prior to said mixing.

* * * * *